(12) United States Patent  
Henderek et al.

(10) Patent No.: US 9,596,391 B2
(45) Date of Patent: Mar. 14, 2017

(54) GAZE BASED DIRECTIONAL MICROPHONE

(71) Applicant: Tobii AB, Danderyd (SE)

(72) Inventors: David Figgins Henderek, Enskede (SE); Mårten Skogö, Danderyd (SE)

(73) Assignee: Tobii AB, Danderyd (SE)

( * ) Notice: Subject to any disclaimer, the term of this patent is extended or adjusted under 35 U.S.C. 154(b) by 0 days.

(21) Appl. No.: 14/452,178

(22) Filed: Aug. 5, 2014

(65) Prior Publication Data

US 2015/0063603 A1    Mar. 5, 2015

Related U.S. Application Data

(60) Provisional application No. 61/873,154, filed on Sep. 3, 2013.

(51) Int. Cl.
| | |
|---|---|
| *H04R 3/00* | (2006.01) |
| *H04N 5/225* | (2006.01) |
| *G06F 3/01* | (2006.01) |
| *G02B 27/01* | (2006.01) |
| *H04R 1/32* | (2006.01) |
| *A61B 3/113* | (2006.01) |

(52) U.S. Cl.
CPC ......... *H04N 5/2254* (2013.01); *A61B 3/113* (2013.01); *G02B 27/017* (2013.01); *G06F 3/013* (2013.01); *H04N 5/2256* (2013.01); *H04R 1/32* (2013.01); *G02B 2027/0138* (2013.01); *G02B 2027/0178* (2013.01); *G02B 2027/0187* (2013.01); *H04R 2201/40* (2013.01)

(58) Field of Classification Search
CPC . H04R 3/00; H04R 3/005; H04R 1/32; H04N 5/2254; H04N 5/2256; A61B 3/113; G06F 3/013

USPC ................................................ 381/122
See application file for complete search history.

(56) References Cited

U.S. PATENT DOCUMENTS

| | | |
|---|---|---|
| 6,204,974 B1 | 3/2001 | Spitzer |
| 6,353,422 B1 | 3/2002 | Perlman et al. |
| 6,577,329 B1 | 6/2003 | Selker et al. |
| 7,306,337 B2 | 12/2007 | Ji et al. |
| 7,380,938 B2 | 6/2008 | Chmielewski et al. |

(Continued)

FOREIGN PATENT DOCUMENTS

| | | |
|---|---|---|
| EP | 2731049 | 5/2014 |
| GB | 2281838 | 3/1995 |

(Continued)

OTHER PUBLICATIONS

Non-Final Office Action for U.S. Appl. No. 14/281,587, mailed Aug. 8, 2014, 23 pages.

(Continued)

*Primary Examiner* — Simon King
(74) *Attorney, Agent, or Firm* — Kilpatrick Townsend & Stockton LLP

(57) ABSTRACT

According to the invention, a system for converting sound to electrical signals is disclosed. The system may include a gaze tracking device and a microphone. The gaze tracking device may determine a gaze direction of a user. The microphone may be more sensitive in a selected direction than at least one other direction and alter the selected direction based at least in part on the gaze direction determined by the gaze tracking device.

23 Claims, 6 Drawing Sheets

(56) References Cited

U.S. PATENT DOCUMENTS

| | | |
|---|---|---|
| 7,549,743 B2 | 6/2009 | Huxlin et al. |
| 7,561,143 B1 | 7/2009 | Milekic |
| 7,572,008 B2 | 8/2009 | Elvesjo et al. |
| 7,806,525 B2 | 10/2010 | Howell et al. |
| 8,066,375 B2 | 11/2011 | Skogö et al. |
| 8,292,433 B2 | 10/2012 | Vertegaal |
| 8,390,533 B2 | 3/2013 | Yamamoto et al. |
| 8,472,120 B2 | 6/2013 | Border et al. |
| 8,487,838 B2 | 7/2013 | Lewis et al. |
| 8,488,246 B2 | 7/2013 | Border et al. |
| 8,500,271 B2 | 8/2013 | Howell et al. |
| 9,041,787 B2 | 5/2015 | Andersson et al. |
| 2002/0105482 A1 | 8/2002 | Lemelson et al. |
| 2005/0175218 A1 | 8/2005 | Vertegaal et al. |
| 2007/0030442 A1 | 2/2007 | Howell et al. |
| 2007/0121066 A1 | 5/2007 | Nashner |
| 2008/0278682 A1 | 11/2008 | Huxlin et al. |
| 2009/0086165 A1 | 4/2009 | Beymer |
| 2009/0122161 A1 | 5/2009 | Bolkhovitinov |
| 2010/0045571 A1 | 2/2010 | Yamamoto et al. |
| 2010/0066975 A1 | 3/2010 | Rehnstrom |
| 2010/0110368 A1 | 5/2010 | Chaum |
| 2010/0198104 A1 | 8/2010 | Schubert et al. |
| 2010/0271587 A1 | 10/2010 | Pavlopoulos |
| 2011/0007277 A1 | 1/2011 | Solomon |
| 2011/0037606 A1 | 2/2011 | Boise |
| 2011/0069277 A1 | 3/2011 | Blixt et al. |
| 2011/0140994 A1 | 6/2011 | Noma |
| 2011/0279666 A1 | 11/2011 | Strömbom et al. |
| 2012/0075168 A1 | 3/2012 | Osterhout et al. |
| 2012/0163606 A1* | 6/2012 | Eronen .......... H04S 7/302 381/22 |
| 2012/0194419 A1 | 8/2012 | Osterhout et al. |
| 2012/0230547 A1 | 9/2012 | Durnell et al. |
| 2012/0235883 A1 | 9/2012 | Border et al. |
| 2012/0235900 A1 | 9/2012 | Border et al. |
| 2012/0288139 A1 | 11/2012 | Singhar |
| 2013/0021373 A1 | 1/2013 | Vaught et al. |
| 2013/0044042 A1 | 2/2013 | Olsson et al. |
| 2013/0050070 A1 | 2/2013 | Lewis et al. |
| 2013/0114043 A1 | 5/2013 | Balan et al. |
| 2013/0163089 A1 | 6/2013 | Bohn |
| 2013/0201080 A1 | 8/2013 | Evans et al. |
| 2013/0257709 A1 | 10/2013 | Raffle et al. |
| 2013/0286178 A1 | 10/2013 | Lewis et al. |
| 2013/0300648 A1* | 11/2013 | Kim .......... G06F 3/011 345/156 |
| 2013/0314303 A1 | 11/2013 | Osterhout et al. |
| 2013/0325463 A1 | 12/2013 | Greenspan et al. |
| 2014/0154651 A1 | 6/2014 | Stack |
| 2014/0160001 A1 | 6/2014 | Kinnebrew et al. |
| 2015/0061995 A1 | 3/2015 | Gustafsson et al. |
| 2015/0061996 A1 | 3/2015 | Gustafsson et al. |
| 2015/0062322 A1 | 3/2015 | Gustafsson et al. |
| 2015/0062323 A1 | 3/2015 | Gustafsson et al. |
| 2015/0063603 A1 | 3/2015 | Henderek et al. |

FOREIGN PATENT DOCUMENTS

| | | |
|---|---|---|
| WO | 2009129222 | 10/2009 |
| WO | 2010085977 | 8/2010 |
| WO | 2013067230 | 5/2013 |
| WO | 2013117727 | 8/2013 |
| WO | 2015034560 | 3/2015 |
| WO | 2015034561 | 3/2015 |

OTHER PUBLICATIONS

Notice of Allowance for U.S. Appl. No. 14/281,587, mailed Jan. 21, 2015, 16 pages.

Non-Final Office Action for U.S. Appl. No. 14/281,599, mailed Oct. 1, 2015, 13 pages.

Ebisawa, "Improved Video-Based Eye-Gaze Detection Method", IEEE Transactions on Instrumentation and Measurement, vol. 47, No. 4, Aug. 1998, 8 pages.

International Search Report and Written Opinion for PCT Application No. PCT/US2014/038651, mailed Oct. 23, 2014, 3 pages.

International Search Report and Written Opinion for PCT Application No. PCT/US2014/038653, mailed Oct. 22, 2014, 3 pages.

Tian et al., "Dynamic visual acuity during transient and sinusoidal yaw rotation in normal and unilaterally vestibulopathic humans", Experimental Brain Research, Springer international DE, vol. 137, No. 1, Mar. 1, 2001, pp. 12-25.

Final Office Action for U.S. Appl. No. 14/281,616, mailed Sep. 8, 2016, 20 pages.

Non-Final Office Action for U.S. Appl. No. 14/281,676, mailed Jun. 13, 2016, 6 pages.

Final Office Action for U.S. Appl. No. 14/281,599, mailed Jul. 14, 2016, 18 pages.

International Preliminary Report on Patentability for PCT Application No. PCT/US2014/038651, mailed Mar. 17, 2016, 6 pages.

International Preliminary Report on Patentability for PCT Application No. PCT/US2014/038653, mailed Mar. 17, 2016, 6 pages.

Non-Final Office Action for U.S. Appl. No. 14/281,616, mailed Feb. 12, 2016, 18 pages.

* cited by examiner

GAZE BASED DIRECTIONAL MICROPHONE

CROSS-REFERENCE TO RELATED APPLICATIONS

This application claims priority to, and the benefit of, U.S. Provisional Patent Application 61/873,154, filed on Sep. 3, 2013, and entitled "PORTABLE EYE TRACKING DEVICE," the entire contents of which are hereby incorporated by reference, for all purposes, as if fully set forth herein.

BACKGROUND OF THE INVENTION

Directional microphones are well known in the art. Such microphones are capable of converting sound received by the microphone into electrical signals, while being more sensitive to sounds from the direction in which they are pointed than from other directions. This allows the directional microphone to be used to pick up sound primarily from specific sources or locations, to the exclusion of sounds from other directions, depending on the direction the microphone is pointed. Examples of such microphones include a shotgun microphone or a parabolic microphone.

In other types of directional microphone systems, arrays of microphones are arranged, and a directionally sensitive effect can be achieved by processing the outputs of the collective array to arrive at a signal representative of the sound received from the desired direction. In some applications, such microphones may be used to 'map' the sound from a general direction, and isolate which specific direction certain sounds are coming from.

However, for each of these types of directional microphones, thoughtful and deliberate input or handling is required by an operator to determine which direction to point or direct the microphone. Embodiments of the invention provide solutions to these and other problems.

BRIEF DESCRIPTION OF THE INVENTION

In one embodiment, a system for converting sound to electrical signals is provided. The system may include a gaze tracking device and a microphone. The gaze tracking device may determine a gaze direction of a user. The microphone may be more sensitive in a selected direction than at least one other direction and alter the selected direction based at least in part on the gaze direction determined by the gaze tracking device.

In another embodiment, a method for converting sound to electrical signals is provided. The method may include determining a gaze direction of a user. The method may also include altering a direction in which a microphone is directed based at least in part on the gaze direction.

In another embodiment, a non-transitory machine readable medium having instructions stored thereon is provided. The instructions are executable by a processor to at least receive, from a gaze tracking device, data representing a gaze direction of a user. The instruction may also be executable to cause a direction in which a microphone is most sensitive to be altered based at least in part on the data representing the gaze direction.

BRIEF DESCRIPTION OF THE DRAWINGS

The present invention is described in conjunction with the appended figures.

Figure 1:
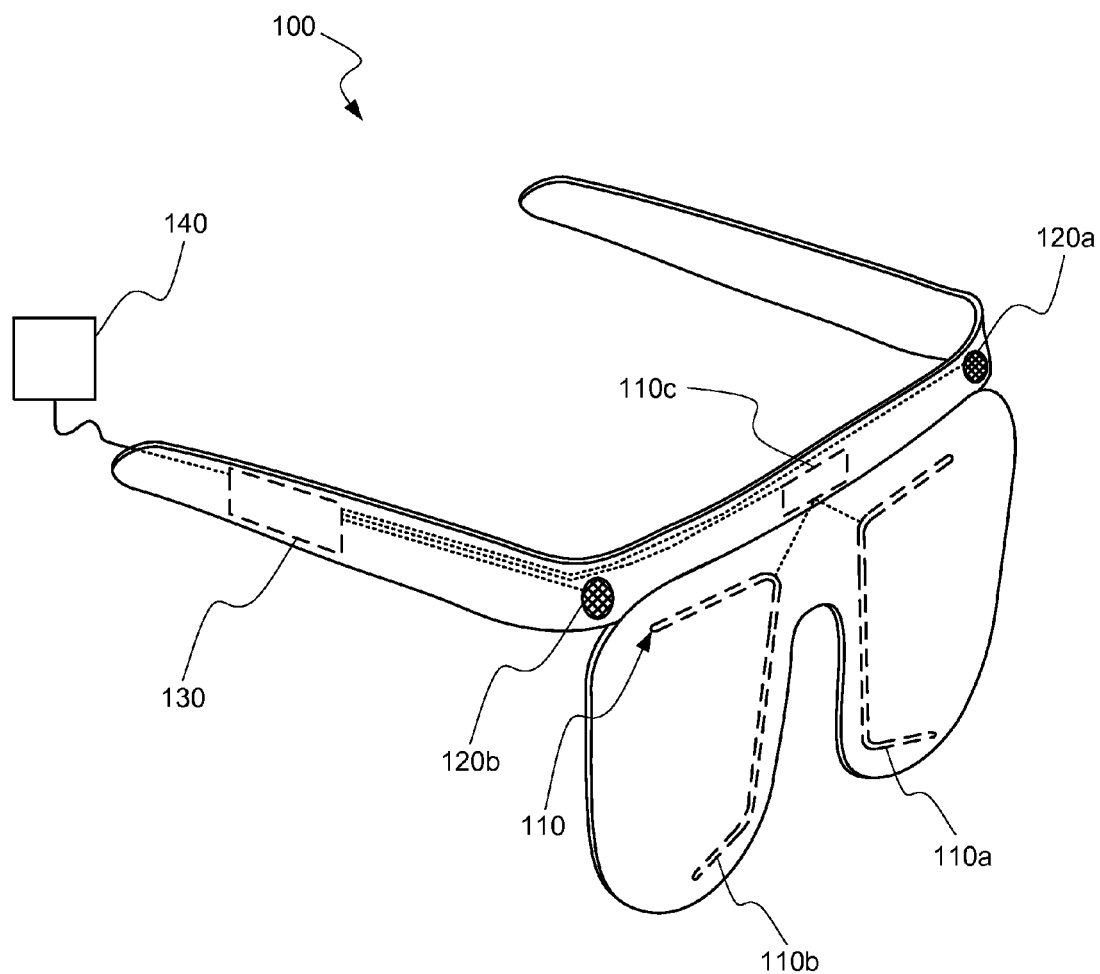
FIG. 1 is an axonometric view of an embodiment of the invention incorporated into eyeglass frames.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims. Any detail present in one discussed embodiment may or may not be present in other versions of that embodiment or other embodiments discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

In one embodiment, a system for converting sound to electrical signals is provided. The system may include a gaze tracking device and a microphone. The gaze tracking device may determine a gaze direction of a user. The microphone may be more sensitive in a selected direction than at least one other direction and alter the selected direction based at least in part on the gaze direction determined by the gaze tracking device.

The gaze tracking device may be any device which is able to detect the direction of the gaze of a user's eyes. Gaze tracking devices and methods, sometimes referred to as gaze detection systems and methods, include, for example, products produced and available from Tobii Technology AB, and which operate by using infrared illumination and an image sensor to detect reflection from the eye of a user. An example of such a gaze detection system is described in U.S. Pat. No. 7,572,008, which is hereby incorporated by reference, for all purposes, as if fully set forth herein. Other alternative gaze detection systems may also be employed by the invention, regardless of the technology behind the gaze detection system. Gaze tracking device may employ its own processor or the processor of another device to interpret and process data received. When a gaze tracking device is referred to herein, both possible methods of processing data are referred to.

The microphone may be any device which converts sounds into an electrical signal. In some embodiments, the microphone may include a plurality of microphones which are oriented in different directions. In some embodiments, one or more of the microphones may be a unidirectional microphone which is more sensitive in one direction than other directions.

In some embodiments, the system may also include an output device. Merely by way of example, the output device may be a speaker, a cochlear implant, or a recording device. In these or other embodiments, the gaze tracking device, the microphone, and/or the output device may be coupled with a frame configured to be worn on a user's head. In some embodiments, this frame may be an eyeglass frame worn by the user, either with or without corrective, assistive, and/or shaded lenses.

The manner in which the gaze direction is determined, and how the microphone is configured to respond may vary in different embodiments. In some embodiments, the gaze tracking device may determine a point in space representative of the gaze direction, and the microphone may be directed toward altering the selected direction such that the selected direction intersects the point in space. In other embodiments, the direction of the microphone may be altered to be parallel with the gaze direction.

While in some embodiments altering the direction of the microphone may include physically reorienting the microphone or microphones, in other embodiments, where a plurality of microphones are employed, unidirectional or otherwise, the outputs of the plurality of microphones may be processed to generate a direction-sensitive output. In one embodiment, where at least two microphones are utilized, processing the outputs may include adding delay to a signal received from a first unidirectional microphone to create a delayed signal, and then summing the delayed signal with a signal received from a second unidirectional microphone. This may result in an output which is more sensitive to sounds received in the direction of the first microphone. A processor in communication with the gaze tracking device and the microphone, which has access to information indicative of the physical location and/or orientation of the microphones, may perform the necessary processing after receiving information from the gaze tracking device.

In some embodiments, additional features may be found on the system which allow a user to control the characteristics of the system. For example, a user input device, perhaps a switch or other control, could be provided to allow the user to selectively enable and disable altering of the selected direction. In another example, a user input device could be provided to allow the user to adjust the sensitivity of the microphone in the selected direction compared to other directions. On/off switches for either directional or ambient sound collection/reproduction could also be provided.

In another embodiment, a system is provided whereby a user may direct their speech, or other sounds made, to a specific person based on where they are gazing. In one embodiment, the system may include a gaze tracking device and at least one microphone. One or both of these components, as well as other components of the embodiment may be disposed on or within a frame, possibly worn by the user. In one example, the frame could be a set of eyeglass frames worn by the user. The gaze tracking device may be any device which is able to detect the direction of the gaze of the user's eyes. The microphone may be configured to receive sound or speech from the user.

In operation, the user's speech is picked up by the microphone while the user's gaze direction is monitored. A processor can determine if a listening device, for example a wireless headset or earphone (i.e., a Bluetooth™ headset), is being used by an individual in the direction of the user's gaze (or in some range around such direction). If so, the processor can direct transmission of the sound and/or speech from the user to the listening device.

Determining whether a listening device is within the direction of the user's gaze may occur prior to or during the user's emitting the sound or speech. For example, the processor may continually monitor the user's gaze direction and determine if a listening device is within the user's gaze direction, and thus be ready to transmit to such devices upon the user emitting sound or speech. Wireless communication directionally limited to the direction of the user's gaze may be used to initiate and continue communication between the system and the listening device. In other embodiments, the processor may only attempt to identify listening device within the gaze direction of the user after sound or speech is emitted by the user. Depending on the embodiment, sounds or speech of the user may continue to be transmitted to the identified listening device for some predefined time after the user's gaze has changed directions, or may cease immediately after the user is no longer gazing in the direction of the identified listening device.

Additionally, the listening devices which are eligible to receive transmissions from the system may be known ahead of time. While any number of potential listening devices may be within the gaze direction of the user, only those in a predefined list of eligible listening devices may be allowed to receive the communication. This may be achieved either by a wireless handshake procedure between the system and the target listening device being necessary at the initiation of communications, or via encryption of the communications such that only eligible listening devices are able to decrypt such communications.

In this manner, a user may communicate with a specific person they are gazing at, and only or primarily that person, regardless of their proximity to the person. This may be helpful where the person is some distance from the user, where the user's vocal capabilities are impaired (i.e., low speech volume), or where the user does not wish others to hear the sound or speech they produce (or at least not hear it as loudly).

Turning now to FIG. 1, an axonometric view of an embodiment of the invention incorporated into eyeglass frames 100 is shown. Eyeglass frames 100, as shown, are merely exemplary, and may take on other designs in other embodiments. Eyeglass frames 100 include a gaze tracking device 110, microphones 120, processor 130, and cabling which enable communication between gaze tracking device 110, microphones 120, and processor 130. In other embodiments, communication between components may be wireless. While in FIG. 1 the components are shown in exemplary locations, in other embodiments the components may be located in different positions.

In this embodiment, gaze tracking device 110 includes eye tracking devices 110a,b, and dedicated processor 110c. Dedicated processor 110c analyzes data received from eye tracking devices 110a,b, and determines the user's gaze direction therefrom. In other embodiments, processor 130 may be used in lieu of dedicated processor 110c.

Microphones 120 may be located in multiple locations of eyeglass frames 100. In this embodiment, microphone 120a is directed to the left side of the user, and microphone 120b is directed to the right side of the user. While in some embodiments microphones 120 may be electro-mechanical, and capable of being physically reoriented in response to a change in gaze direction as discussed herein, for the sake of further discussion, it will be assumed that microphones 120 are stationary, and that processor 130 processes the outputs thereof to deliver a directional output.

An output device 140 is shown in block form, and represents any number of potential output devices for the system. Merely by way of example, output device 140 may include a speaker, for example one found in an earphone or headset; a cochlear implant of the user, or a recording device such as an MP3 device, mobile phone, tablet, computer, etc. Output provided by processor 130, or directly from microphones, could be provided to output device 140 during use of the system. While output device 140 is shown here in physical communication with processor 130, in other embodiments, output device 130 may be in wireless communication with processor 130 or other elements of the system.

Figure 2A:
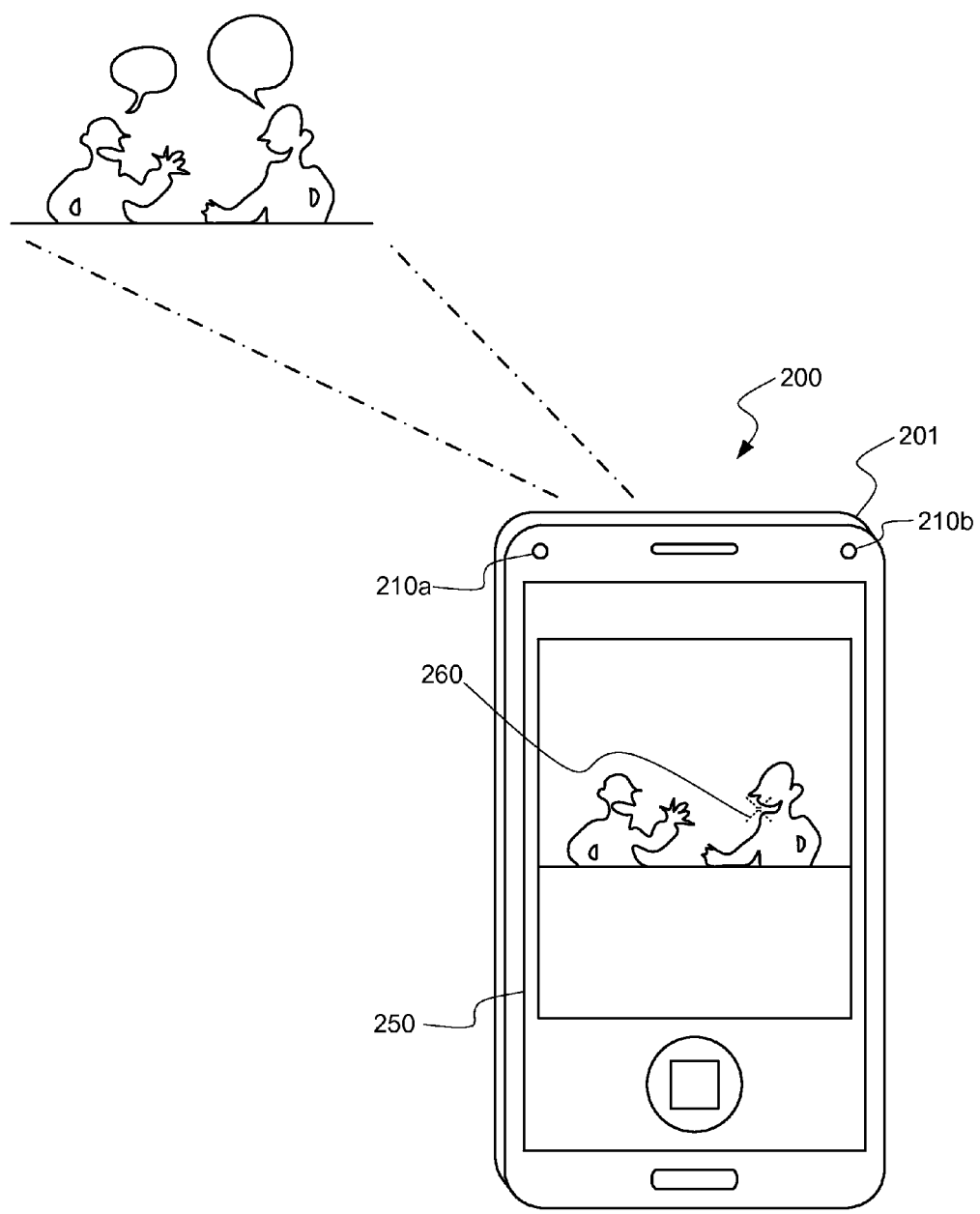
FIG. 2A is a front view of another embodiment of the invention incorporated into a mobile device.
Figure 2B:
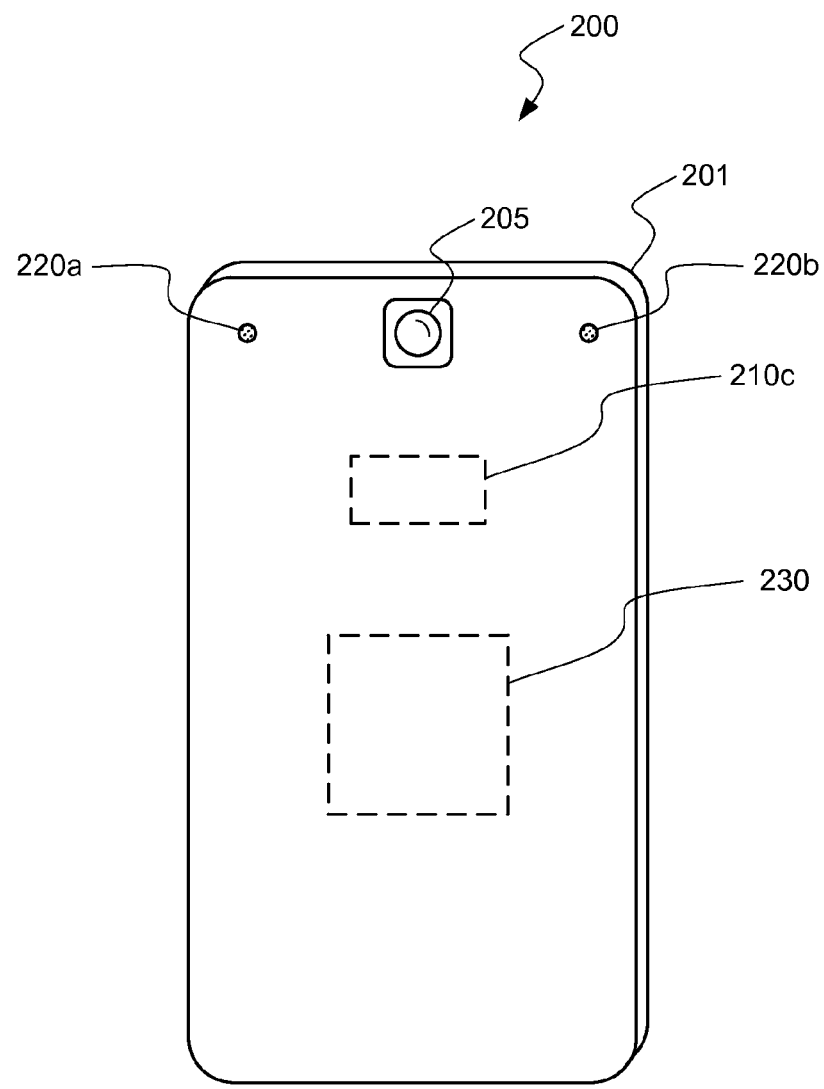
FIG. 2B is a back view of the embodiment of FIG. 2A.

FIGS. 2A & 2B are schematic diagrams of another embodiment 200 in which a mobile device 201 employs systems and methods of the invention. FIG. 2A shows the front of mobile device 201, while FIG. 2B shows the back of mobile device 201. Mobile device 201, which could also be a video recording device, a tablet computer, a notebook/laptop computer, a desktop computer, or other device, includes a camera 205, gaze tracking device 210, microphones 220, processor 230, and display screen 250 (or other type of display device). In this embodiment, gaze tracking device 210, may include an eye tracking devices 210a,b, and dedicated processor 210c. Dedicated processor 210c analyzes data received from eye tracking devices 210a,b, and determines the user's gaze direction therefrom. In other embodiments, processor 230 may be used in lieu of dedicated processor 210c.

During use, a user employs camera 205 to observe a scene, and the scene is reproduced on display screen 250. In some embodiments, the scene may be recorded and stored on mobile device 201. While the user views display screen 250, gaze tracking device 210 determines where the user's gaze point is located on display screen 250. In some embodiments, a marker 260, shown here as a dotted—'X,' may be displayed on the screen to reflect the determined gaze point. Mobile device 201 may then process signals received by microphones 220, as discussed herein, to create a directionally sensitive signal representative of sounds coming from the direction corresponding to the determined user's gaze.

Thus, in the example shown, the user's gaze is located on the speaker to the right in the scene viewed from the camera. Gaze tracking device 210 would determine this, and processor 230 would cause display screen 250 to reproduce marker 260 at the location of the user's gaze. Microphones 220 would receive sound from the scene, and processor 230 would then process signals from microphones 220 to create a signal which is more directionally sensitive toward the right speaker (more specifically, toward the location in the scene which corresponds to the user's gaze point on display device 250). This directionally sensitive sound can be reproduced immediately by a speaker or other output device on mobile device 201, or stored, perhaps with the accompanying video, for later use.

Figure 3:
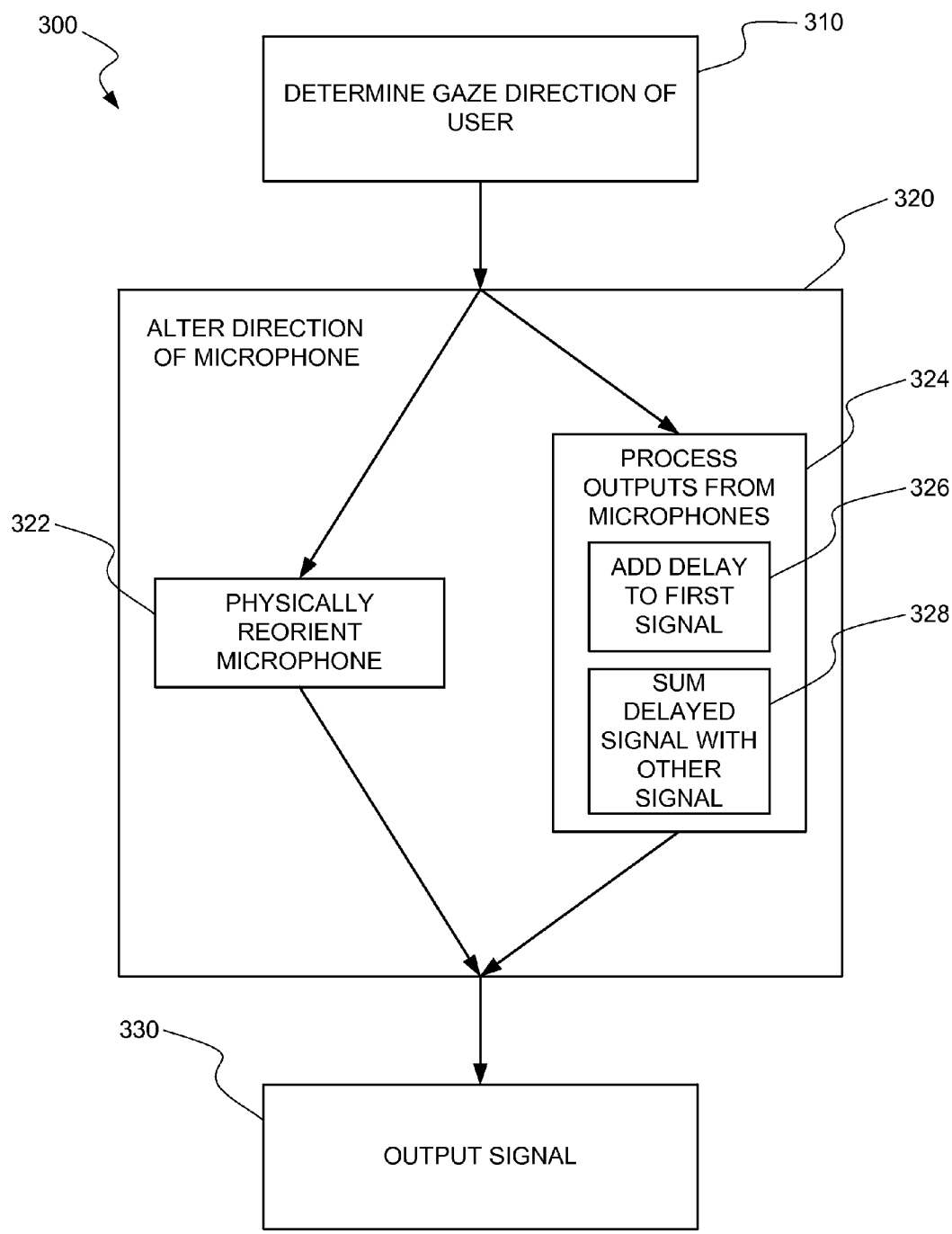
FIG. 3 is a block diagram of a method of the invention.

FIG. 3 is a block diagram of a method 300 of the invention, as potentially performed by the system shown in FIG. 1. At block 310, using gaze tracking device 110, 210, the gaze direction of a user is determined. Depending on the embodiment, processor 130, 230 may also assist in analyzing data collected by gaze tracking device 110, 210 to determine the gaze direction.

At block 320, the direction of microphones 120, 220 is altered in response to changes in the gaze direction of the user. Depending on the embodiment, microphones 120, 220 may be physically reoriented at block 322, or outputs from multiple stationary microphones 120, 220 may be processed to deliver directional sensitivity at block 324. When multiple stationary microphones 120, 220 are used, at block 326, delay may be added to a signal received from a microphone 120, 220 more relatively directed toward the gaze direction as another microphone 120, 220. At block 328, the delayed signal may be summed with a signal received from a microphone 120, 220 not as relatively directed toward the gaze direction to create a directionally sensitive signal.

Those of skill in the art will recognize various other algorithms which may be used to generate a directional sensitive output from multiple microphones 120, 220 when the direction from which sound is desired to be produced (i.e., the gaze direction) is known. At block 330, the new signal is outputted.

Figure 4A:
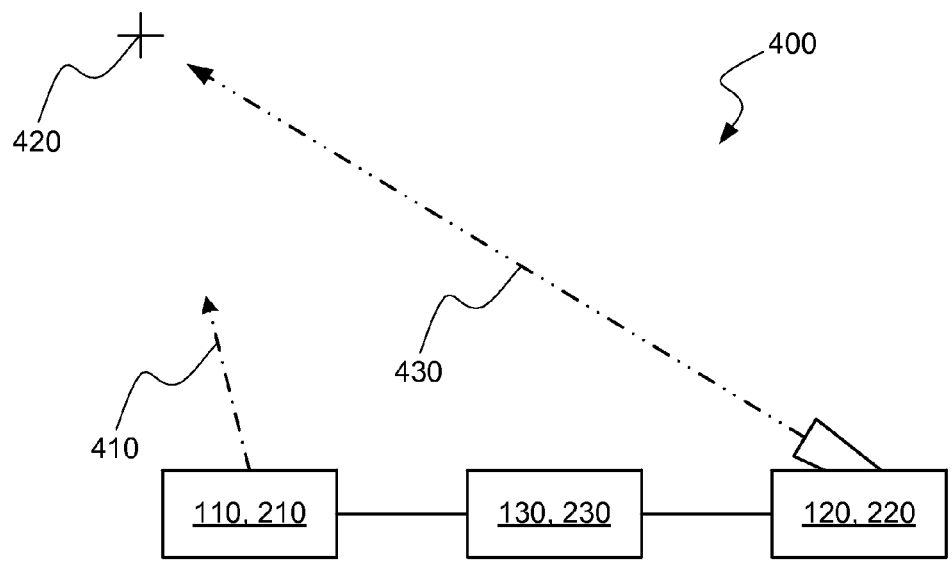
FIG. 4A is a schematic diagram of one method of altering the directional sensitivity of a microphone in response to a change in gaze direction.

FIG. 4A is a schematic diagram 400 of one method of altering the directional sensitivity of a microphone 120, 220 in response to a change in gaze direction. In this method, processor 130, 230 receives data from gaze tracking device 110, 210 which indicates a gaze direction 410. Processor 130, 230 determines that the user is looking at a point-in-space 420, and then either (1) instructs microphone 120, 220 to direct itself toward point-in-space 420 (or a corresponding direction indicated by arrow 430), or (2) processes information from a microphone array, represented by microphone 120, 220, to create a directionally sensitive output representative of the sound received from point-in-space 420 (or from the corresponding direction indicated by arrow 430).

Figure 4B:
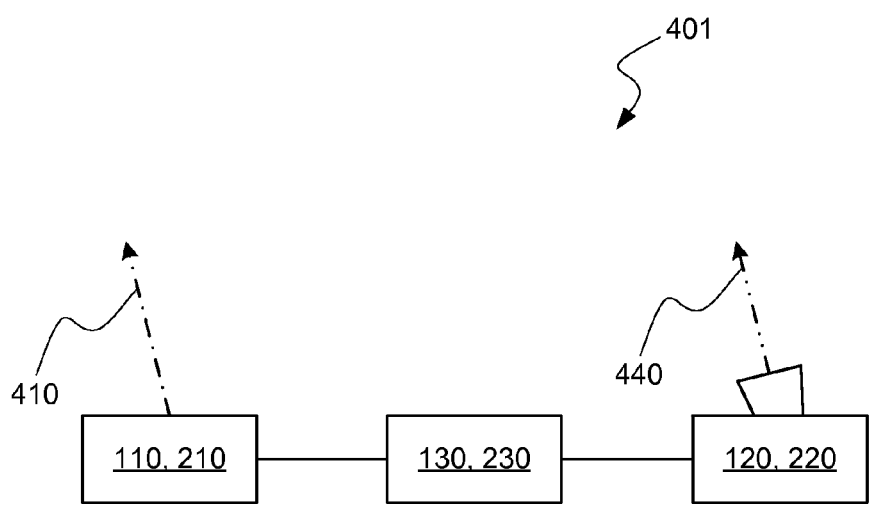
FIG. 4B is a schematic diagram of another method of altering the directional sensitivity of a microphone in response to a change in gaze direction.

FIG. 4B is a schematic diagram 401 of another method of altering the directional sensitivity of a microphone 120, 220 in response to a change in gaze direction. In this method, processor 130, 230 receives data from gaze tracking device 110, 210 which indicates a gaze direction 410. Processor 130, 230 then either (1) instructs microphone 120, 220 to direct itself in a parallel direction to gaze direction 410, as indicated by arrow 440, or (2) processes information from a microphone array, represented by microphone 120, 220, to create a directionally sensitive output representative of the sound received from direction 440.

Figure 5:
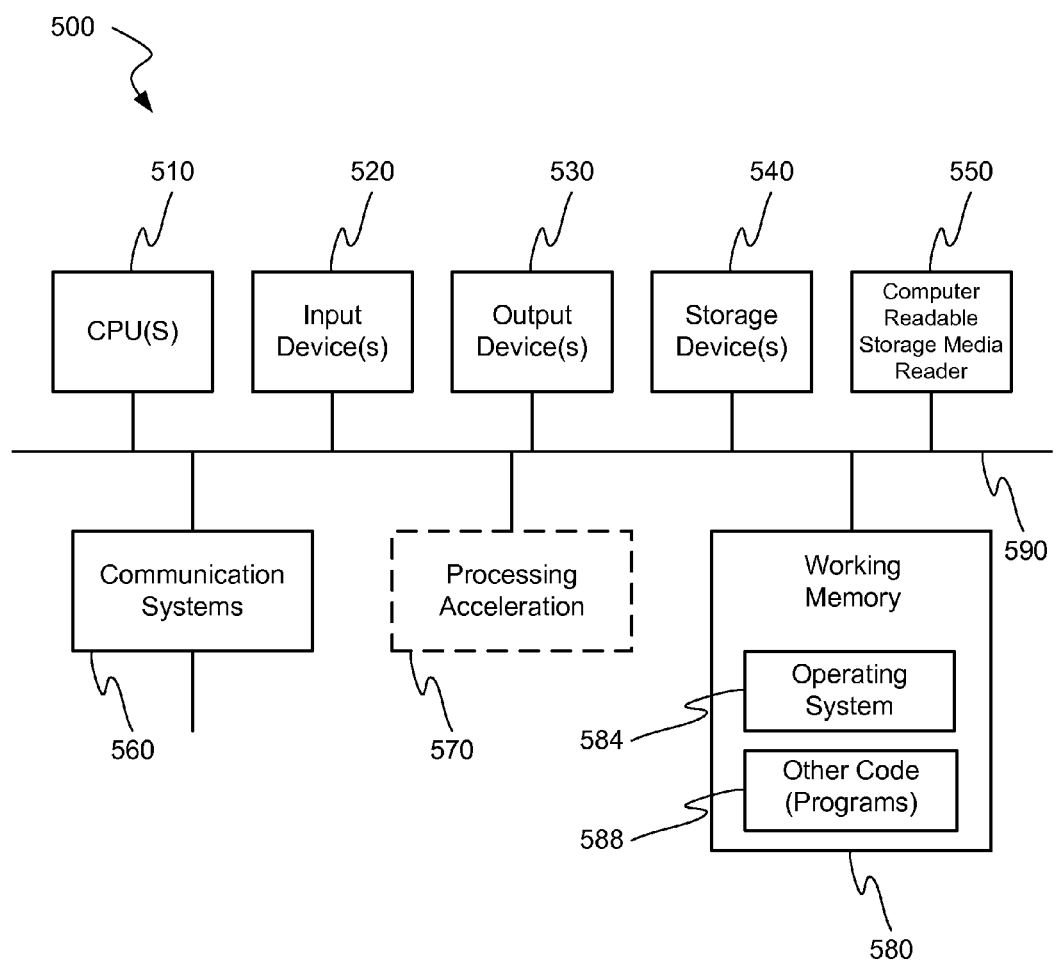
FIG. 5 is a block diagram of an exemplary computer system capable of being used in at least some portion of the apparatuses or systems of the present invention, or implementing at least some portion of the methods of the present invention.

FIG. 5 is a block diagram illustrating an exemplary computer system 500 in which embodiments of the present invention may be implemented. This example illustrates a computer system 500 such as may be used, in whole, in part, or with various modifications, to provide the functions of gaze tracking device 110, microphones 120, processor 130, output device 140, and/or other components of the invention such as those discussed above. For example, various functions of gaze tracking device 110 or processor 130 may be controlled by the computer system 500, including, merely by way of example, determining a user's gaze direction, determining a direction to orient microphones, processing signals received from microphones, etc.

The computer system 500 is shown comprising hardware elements that may be electrically coupled via a bus 590. The hardware elements may include one or more central processing units 510, one or more input devices 520 (e.g., a mouse, a keyboard, etc.), and one or more output devices 530 (e.g., a display device, a printer, etc.). The computer system 500 may also include one or more storage device 540. By way of example, storage device(s) 540 may be disk drives, optical storage devices, solid-state storage device such as a random access memory ("RAM") and/or a read-only memory ("ROM"), which can be programmable, flash-updateable and/or the like.

The computer system 500 may additionally include a computer-readable storage media reader 550, a communications system 560 (e.g., a modem, a network card (wireless or wired), an infra-red communication device, Bluetooth™ device, cellular communication device, etc.), and working memory 580, which may include RAM and ROM devices as described above. In some embodiments, the computer system 500 may also include a processing acceleration unit 570, which can include a digital signal processor, a special-purpose processor and/or the like.

The computer-readable storage media reader 550 can further be connected to a computer-readable storage medium, together (and, optionally, in combination with storage device(s) 540) comprehensively representing remote, local, fixed, and/or removable storage devices plus storage media for temporarily and/or more permanently containing computer-readable information. The communications system 560 may permit data to be exchanged with a network, system, computer and/or other component described above.

The computer system 500 may also comprise software elements, shown as being currently located within a working memory 580, including an operating system 584 and/or other code 588. It should be appreciated that alternate embodiments of a computer system 500 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 500 may include code 588 for implementing any or all of the function of the various elements of the architecture as described herein. For example, software, stored on and/or executed by a computer system such as system 500, can provide the functions of gaze tracking device 110, microphones 120, processor 130, output device 140, and/or other components of the invention such as those discussed above. Methods implementable by software on some of these components have been discussed above in more detail.

The invention has now been described in detail for the purposes of clarity and understanding. However, it will be appreciated that certain changes and modifications may be practiced within the scope of the appended claims.

What is claimed is:

1. A system for converting sounds to electrical signals, wherein the system comprises:
    a gaze tracking device, wherein the gaze tracking device determines a gaze direction of a user;
    a microphone;
    a camera;
    a display device reproducing a scene captured by the camera, wherein:
        the microphone is more sensitive in a selected direction than at least one other direction;
        the microphone alters the selected direction based at least in part on the gaze direction determined by the gaze tracking device;
        the gaze tracking device determining the gaze direction of the user comprises determining a gaze point of the user on the display device; and
        the microphone altering the selected direction based at least in part on the gaze direction determined by the gaze tracking device comprises the microphone altering the selected direction towards a direction in the scene corresponding to the gaze point of the user on the reproduced scene.

2. The system for converting sounds to electrical signals of claim 1, wherein the system further comprises:
    an output device.

3. The system for converting sounds to electrical signals of claim 2, wherein the output device comprises a selection from a group consisting of:
    a speaker;
    a cochlear implant; and
    a recording device.

4. The system for converting sounds to electrical signals of claim 1, wherein the microphone altering the selected direction based at least in part on the gaze direction comprises:
the gaze tracking device determining a point in space representative of the gaze direction; and
the microphone altering the selected direction such that the selected direction intersects the point in space.

5. The system for converting sounds to electrical signals of claim 1, wherein the microphone altering the selected direction based at least in part on the gaze direction comprises:
the microphone altering the selected direction to be parallel with the gaze direction.

6. The system for converting sounds to electrical signals of claim 1, wherein the system further comprises:
a frame configured to be worn on the user's head, wherein the eye tracking device is coupled with the frame.

7. The system for converting sounds to electrical signals of claim 6, wherein:
the microphone is coupled with the frame.

8. The system for converting sounds to electrical signals of claim 1, wherein the microphone altering the selected direction comprises:
physically reorienting the microphone.

9. The system for converting sounds to electrical signals of claim 1, wherein:
the microphone comprises a plurality of unidirectional microphones; and
the microphone altering the selected direction comprises:
processing outputs from the plurality of unidirectional microphones.

10. The system for converting sounds to electrical signals of claim 9, wherein processing outputs from the plurality of unidirectional microphones comprises:
adding delay to a signal received from a first unidirectional microphone to create a delayed signal
summing a signal received from a second unidirectional microphone with the delayed signal, wherein the second unidirectional microphone is relatively less aligned with the selected direction than the first unidirectional microphone.

11. The system for converting sounds to electrical signals of claim 1, wherein the system further comprises:
a user input device configured to allow the user to selectively enable and disable altering of the selected direction.

12. The system for converting sounds to electrical signals of claim 1, wherein the system further comprises:
a user input device configured to allow the user to adjust the sensitivity of the microphone in the selected direction compared to other directions.

13. A method for converting sounds to electrical signals, wherein the method comprises:
reproducing a scene captured by a camera on a display device;
determining a gaze direction of a user with a gaze tracking device, wherein determining the gaze direction comprises determining a gaze point of the user on the display device; and
altering, with a processor, a direction in which a microphone is directed based at least in part on the gaze direction, wherein altering the direction in which the microphone is directed based at least in part on the gaze direction comprises altering the direction towards a direction in the scene corresponding to the gaze point of the user on the reproduced scene.

14. The method for converting sounds to electrical signals of claim 13, wherein altering the direction in which the microphone is directed comprises:
physically reorienting the microphone.

15. The method for converting sounds to electrical signals of claim 13, wherein:
the microphone comprises a plurality of unidirectional microphones; and
altering the direction in which the microphone is directed comprises:
processing outputs from the plurality of unidirectional microphones.

16. The method for converting sounds to electrical signals of claim 15, wherein processing outputs from the plurality of unidirectional microphones comprises:
adding delay to a signal received from a first unidirectional microphone to create a delayed signal
summing a signal received from a second unidirectional microphone with the delayed signal, wherein the second unidirectional microphone is relatively less aligned with the selected direction than the first unidirectional microphone.

17. A non-transitory machine readable medium having instructions stored thereon, wherein instructions are executable by a processor to at least:
reproduce a scene captured by a camera on a display device;
receive, from a gaze tracking device, data representing a gaze direction of a user;
determining the gaze direction of the user from the data, wherein determining the gaze direction comprises determining a gaze point of the user on the display device; and
cause a direction in which a microphone is most sensitive to be altered based at least in part on the data representing the gaze direction, wherein causing the direction in which the microphone is most sensitive to be altered based at least in part on the data comprises altering the direction in which the microphone is most sensitive towards a direction in the scene corresponding to the gaze point of the user on the reproduced scene.

18. The non-transitory machine readable medium of claim 17, wherein causing the direction in which the directional microphone is most sensitive to be altered comprises:
causing the microphone to be physically reoriented.

19. The non-transitory machine readable medium of claim 17, wherein:
the microphone comprises a plurality of unidirectional microphones; and
causing the direction in which the microphone is most sensitive to be altered comprises:
processing outputs from the plurality of unidirectional microphones.

20. The non-transitory machine readable medium of claim 19, wherein processing outputs from the plurality of unidirectional microphones comprises:
adding delay to a signal received from a first unidirectional microphone to create a delayed signal
summing a signal received from a second unidirectional microphone with the delayed signal, wherein the second unidirectional microphone is relatively less aligned with the selected direction than the first unidirectional microphone.

21. A system for converting sounds to electrical signals, wherein the system comprises:
a gaze tracking device, wherein the gaze tracking device determines a gaze direction of a user; and a microphone, wherein:
the microphone is more sensitive in a selected direction than at least one other direction;
the microphone alters the selected direction based at least in part on the gaze direction determined by the gaze tracking device;
the microphone comprises a plurality of unidirectional microphones;
the microphone altering the selected direction comprises processing outputs from the plurality of unidirectional microphones; and
processing outputs from the plurality of unidirectional microphones comprises:
adding delay to a signal received from a first unidirectional microphone to create a delayed signal; and
summing a signal received from a second unidirectional microphone with the delayed signal, wherein the second unidirectional microphone is relatively less aligned with the selected direction than the first unidirectional microphone.

22. A method for converting sounds to electrical signals, wherein the method comprises:
determining a gaze direction of a user; and
altering a direction in which a microphone is directed based at least in part on the gaze direction, wherein:
the microphone comprises a plurality of unidirectional microphones;
altering the direction in which the microphone is directed comprises processing outputs from the plurality of unidirectional microphones; and
processing outputs from the plurality of unidirectional microphones comprises:
adding delay to a signal received from a first unidirectional microphone to create a delayed signal; and
summing a signal received from a second unidirectional microphone with the delayed signal, wherein the second unidirectional microphone is relatively less aligned with the selected direction than the first unidirectional microphone.

23. A non-transitory machine readable medium having instructions stored thereon, wherein instructions are executable by a processor to at least:
receive, from a gaze tracking device, data representing a gaze direction of a user; and
cause a direction in which a microphone is most sensitive to be altered based at least in part on the data representing the gaze direction, wherein:
the microphone comprises a plurality of unidirectional microphones;
causing the direction in which the microphone is most sensitive to be altered comprises processing outputs from the plurality of unidirectional microphones; and
processing outputs from the plurality of unidirectional microphones comprises:
adding delay to a signal received from a first unidirectional microphone to create a delayed signal; and
summing a signal received from a second unidirectional microphone with the delayed signal, wherein the second unidirectional microphone is relatively less aligned with the selected direction than the first unidirectional microphone.

\* \* \* \* \*